United States Patent [19]

Tobert

[11] Patent Number: 4,929,437

[45] Date of Patent: May 29, 1990

[54] COENZYME $Q_{10}$ WITH HMG-COA REDUCTASE INHIBITORS

[75] Inventor: Jonathan A. Tobert, Maplewood, N.J.

[73] Assignee: Merck & Co., Inc., Rahway, N.J.

[21] Appl. No.: 305,140

[22] Filed: Feb. 2, 1989

[51] Int. Cl.$^5$ ............... A61K 45/00; A61K 31/405; A61K 31/35; A61K 31/12

[52] U.S. Cl. ............... 424/10; 514/415; 514/460; 514/690; 514/922

[58] Field of Search ............... 424/10; 514/415, 690, 514/460, 922

[56] References Cited

U.S. PATENT DOCUMENTS 4,654,373  3/1987  Bertelli ............... 514/690
4,713,397  12/1987  Hirama et al. ............... 514/690

OTHER PUBLICATIONS

Grundy, Scott M. (1988) New Eng. J. of Med 319(1):24–33 "HMG–CoA Reductase Inhibitors for Treatment of Hypercholesterolemia".
J. A. Tobert, Am. J. Cardiol., 1988, 62, 28J–34J.
M. S. Brown, J. Goldstein, J. Lipid Res., 21, 50S (1980).
J. S. MacDonald, Am J. Cardiol., 1988, 62, 16J–27J.
Effects of an Inhibitor of 3–Hydroxy–3–Methylglutaryl Coenzyme A Reductase on Serum Lipoproteins ..., H. Mabuchi, M.D. et al, New Eng. J. Med., 8/27/81.
Biochemical Rationale and Myocardial Tissue Data on the Effective Therapy of Cardiomyopathy with Coenzyme $Q_{10}$, K. Folker et al., Proc. Natl. Acad. Sci. 82, pp. 901–904, Feb. 1985.
Biochemical Rationale and the Cardiac Response of Patients with Muscle Disease to Therapy with Coenzyme $Q_{10}$, Proc. Natl. Acad. Sci., 82, pp. 4513–4516, Jul. 1985, K. Folkers et al.
Multivalent Feedback Regulation of HMG CoA Reductase, A Control Mechanism Coordinating Isoprenoid Synthesis and Cell Growth, J. Lipid Resarch, 21, pp. 505–517, 1980.

Primary Examiner—Douglas W. Robinson
Assistant Examiner—Raymond J. Henley, III
Attorney, Agent, or Firm—Melvin Winokur; Joseph F. DiPrima

[57] ABSTRACT

A pharmaceutical composition and method of counteracting HMG-CoA reductase inhibitor-associated elevated transaminase levels is disclosed. The method comprises the adjunct administration of an effective amount of a HMG-CoA reductase inhibitor and an effective amount of Coenzyme $Q_{10}$.

2 Claims, No Drawings

COENZYME $Q_{10}$ WITH HMG-COA REDUCTASE INHIBITORS

BACKGROUND OF THE INVENTION

HMG-CoA reductase inhibitors represent a new class of cholesterol lowering drugs. Relatively low levels of these drugs effectively reduce plasma cholesterol levels. These drugs are believed to function by inhibiting the chemical transformation HMG-CoA to mevalonate, which is an early and rate-limiting step in the biosynthesis of cholesterol.

In general there have been very few clinical problems with the use of the HMG reductase inhibitors. The most serious reported adverse effects of lovastatin, a commercially available HMG-CoA reductase inhibitor, are myopathy and asymptomatic but marked and persistent increases in liver transaminases. A method of treating HMG-CoA reductase inhibitor-associated myopathy is discussed in copending patent application Ser. No. 298,535 filed, Jan. 18, 1989. About 1.9% of the patients treated with lovastatin in clinical trials have had asymptomatic but marked and persistent transaminase increases, particularly serum glutamic pyruvic transaminase, J. A. Tobert, Am J. Cardiol., 1988, 62: 28J–34J. The elevated transaminase level is reversible upon discontinuance of the therapy.

A branch of the mevalonate cholesterol biosynthetic pathway in mammalian cells leads to the formation of Coenzyme $Q_{10}$ [reviewed by Brown and Goldstein, J. Lipid Res., 21 505 1980]. Coenzyme $Q_{10}$ (2,3-dimethoxy-5-methyl-6-decaprenyl-1, 4-benzoquinone) is a redox component in the respiratory chain and is found in all cells having mitochondria. It is thus an essential co-factor in the generation of metabolic energy and may be important in liver function. J. S. MacDonald et al. have reported (Am. J. Cardiol 1988; 62 6J–27J) that co-administration of mevalonate, with lovastatin in rabbits, rats and dogs, prevents the increases in transaminase levels. This result demonstrates that the transaminase increase produced by lovastatin and other HMG-CoA reductase inhibitors is a direct consequence of inhibition of mevalonate synthesis.

Although cholesterol-lowering therapy through the use of HMG-CoA reductase inhibitors is generally free of side reactions, it would be of considerable benefit to counteract the increased transaminase levels observed in a small number of patients.

DETAILED DESCRIPTION OF THE INVENTION

The present invention relates to a method of counteracting HMG-CoA reductase inhibitor-associated liver damage in a patient receiving HMG-CoA reductase therapy which comprises the adjunct administration of an effective amount of an HMG-CoA reductase inhibitor and an effective amount of Coenzyme $Q_{10}$. In particular, this invention relates to a method of counteracting HMG-CoA reductase inhibitor-associated elevated transaminase levels.

The HMG-CoA reductase inhibitor employed may be lovastatin, simvastatin, pravastatin, XU-62-320(Sodium 3,5-dihydroxy-7 [3–(4-fluorophenyl)-1(methylethyl)-1H-Indole-2yl]-hept-6-enoate) or any other member of the class of compounds that inhibit HMG-CoA reductase. The preparation of lovastatin (U.S. Pat. No. 4,231,938), simvastatin (U.S. Pat. No. 4,444,784) and pravastatin (U.S. Pat. No. 4,346,227) have been described in the patent literature. The preparation of XU-62-320 is described in WIPO Patent WO84/02131, published June 7, 1984. These methods of preparation are hereby incorporated by reference.

Coenzyme $Q_{10}$ is manufactured by the Kanegafuchi Chemical Industry Co., Ltd. and is widely available.

In its application to the counteraction of liver damage and, in particular, elevated transaminase levels, the present invention is accordingly to be understood as providing for the avoidance of liver damage and elevated transaminase levels where this may otherwise occur as well as the amelioration of said damage and elevated transaminase. The term counteracting is accordingly to be understood as connecting both a precautionary or prophylactic as well as curative or treatmental function.

In accordance with the method of the present invention, an HMG-CoA reductase inhibitor and $CoQ_{10}$ can be administered separately at different times during the course of therapy or concomitantly in divided or single combination forms. Thus treatment with $CoQ_{10}$ can commence prior to, subsequent to or concurrent with the commencement of HMG-CoA reductase treatment. The present invention is to be understood as embracing all such regimes of treatment and the term "adjunct administration" is to be interpreted accordingly.

The compounds of the instant invention may be administered orally or parenterally in the form of a capsule, a tablet, an injectable preparation or the like. The general amounts of HMG-CoA reductase inhibitor will be of the same or similar order to that employed in HMG-CoA reductase therapy. In general, satisfactory results are obtained by administration of 10 to 80 mg/day of the HMG-CoA reductase inhibitor in a single or divided dose. Doses of $CoQ_{10}$ may vary from 25 mg to 1 g day in a single or divided dose. Tablets or capsules may also be administered which contain both compounds in the dosage ranges indicated.

EXAMPLE 1

As a specific embodiment of a composition of this invention, 20 mg of lovastatin and 35 mg of Coenzyme $Q_{10}$ are formulated with sufficient finely-divided lactose to provide a total amount of 580 to 590 mg to fill a size 0 hard-gelatin capsule. Optionally added are an excipient such as finely divided cellulose, a disintegrant such as Explotat and a lubricant such as magnesium stearate.

What is claimed is:

1. A method of counteracting HMG-CoA reductase inhibitor-associated elevated transaminase levels in a subject in need of such treatment which comprises the adjunct administration of an effective amount of HMG-CoA reductase inhibitor and an effective amount of Coenzyme $Q_{10}$.

2. A method of claim 1 in which the HMG-CoA reductase inhibitor is selected from the group consisting of: lovastatin, simvastatin, pravastatin and sodium-3,5-dihydroxy-7-[3-(4-fluorophenyl)-1-(methylethyl)-1H-indole-2-yl]-hept-6-enoate.

* * * * *